United States Patent
Funk et al.

(10) Patent No.: US 8,420,773 B2
(45) Date of Patent: Apr. 16, 2013

(54) PROCESS FOR PRODUCING WATER-ABSORBING POLYMER PARTICLES

(75) Inventors: Rüdiger Funk, Niedernhausen (DE); Thomas Pfeiffer, Boehl-Iggelheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/463,545

(22) Filed: May 3, 2012

(65) Prior Publication Data

US 2012/0283401 A1 Nov. 8, 2012

Related U.S. Application Data

(60) Provisional application No. 61/483,088, filed on May 6, 2011.

(51) Int. Cl.
C08G 64/00 (2006.01)
C08G 63/02 (2006.01)

(52) U.S. Cl.
USPC .......................................................... 528/502

(58) Field of Classification Search .................. 528/502
See application file for complete search history.

(56) References Cited

U.S. PATENT DOCUMENTS

| 2010/0272998 A1 | 10/2010 | Weismantel et al. |
| 2011/0251353 A1 | 10/2011 | Funk |
| 2012/0041152 A1 | 2/2012 | Funk et al. |

FOREIGN PATENT DOCUMENTS

| WO | WO-03/004450 A1 | 1/2003 |
| WO | WO-2009/077376 A1 | 6/2009 |
| WO | WO-2010/066680 A2 | 6/2010 |
| WO | WO-2010/124954 A1 | 11/2010 |

OTHER PUBLICATIONS

Buchholz, Fredric L., et al. *Modern Superabsorbent Polymer Technology*, "Solution Polymerization: Unit Operations and Their Effect on Product Quality." New York: John Wiley & Sons, Inc., 1998, pp. 71-103.

*Primary Examiner* — Terressa Boykin
(74) *Attorney, Agent, or Firm* — Marshall, Gerstein & Borun LLP

(57) ABSTRACT

A process for producing water-absorbing polymer particles, comprising polymerization of a monomer solution or suspension, drying the resulting polymer gel, and grinding and classifying the dried polymer gel, wherein the grinding is performed by means of a multistage roll mill, the first milling gap has a width of 500 to 5000 μm, the product mass flow passing through the first milling gap is conducted through a magnetic separator to the second milling gap, and the second milling gap has a smaller gap width than the first milling gap.

10 Claims, No Drawings

PROCESS FOR PRODUCING WATER-ABSORBING POLYMER PARTICLES

CROSS-REFERENCE TO RELATED APPLICATIONS

This application claims the benefit of U.S. Provisional Patent Application No. 61/483,088, filed May 6, 2011, incorporated herein by reference in its entirety.

The present invention relates to a process for producing water-absorbing polymer particles, comprising polymerization of a monomer solution or suspension, drying the resulting polymer gel, and grinding and classifying the dried polymer gel, wherein the grinding is performed by means of a multistage roll mill, the first milling gap has a width of 500 to 5000 µm, the product mass flow passing through the first milling gap is conducted through a magnetic separator to the second milling gap, and the second milling gap has a smaller gap width than the first milling gap.

Water-absorbing polymer particles are used to produce diapers, tampons, sanitary napkins and other hygiene articles, but also as water-retaining agents in market gardening. The water-absorbing polymer particles are also referred to as superabsorbents.

The production of water-absorbing polymer particles is described in the monograph "Modern Superabsorbent Polymer Technology", F. L. Buchholz and A. T. Graham, Wiley-VCH, 1998, pages 71 to 103.

The properties of the water-absorbing polymer particles can be adjusted, for example, via the amount of crosslinker used. With an increasing amount of crosslinker, the centrifuge retention capacity (CRC) falls and the absorption under a pressure of 21.0 g/cm$^2$ (AUL0.3 psi) passes through a maximum.

To improve the use properties, for example, permeability of the swollen gel bed (SFC) in the diaper and absorption under a pressure of 49.2 g/cm$^2$ (AUL0.7 psi), water-absorbing polymer particles are generally surface postcrosslinked. This increases the crosslinking of the particle surface, which can at least partly decouple the absorption under a pressure of 49.2 g/cm$^2$ (AUL0.7 psi) and the centrifuge retention capacity (CRC). This surface postcrosslinking can be performed in aqueous gel phase. Preferably, however, dried, ground and sieved polymer particles (base polymer) are surface coated with a surface postcrosslinker and thermally surface postcrosslinked. Crosslinkers suitable for that purpose are compounds which can form covalent bonds to at least two carboxylate groups of the water-absorbing polymer particles.

The removal of metallic impurities is described in WO 03/004450 A1, WO 2009/077376 A1, WO 2010/066680 A2 and WO 2010/124954 A1.

It was an object of the present invention to provide an improved process for producing water-absorbing polymer particles, especially for improved removal of metal impurities before grinding.

The object was achieved by a process for producing water-absorbing polymer particles by polymerizing a monomer solution or suspension comprising a) at least one ethylenically unsaturated monomer which bears acid groups and may be at least partly neutralized,
b) at least one crosslinker,
c) at least one initiator,
d) optionally one or more ethylenically unsaturated monomers copolymerizable with the monomers mentioned under a) and
e) optionally one or more water-soluble polymers, drying the resulting polymer gel, and grinding and classifying the dried polymer gel, wherein the grinding is performed by means of a multistage roll mill, the first milling gap (coarse roll mill) has a width of 500 to 5000 µm, the product mass flow passing through the first milling gap is conducted through a magnetic separator to the second milling gap, and the second milling gap has a smaller gap width than the first milling gap.

The first milling gap preferably has a gap width of 700 to 3000 µm, more preferably of 850 to 2500 µm, very particularly of 1000 to 2000 µm.

The magnetic separators usable in the process according to the invention are not subject to any restriction.

The magnets used typically have a magnetic flux density of at least 0.6 T, more preferably of at least 0.9 T, most preferably of at least 1.1 T.

The magnetic separator is preferably a channel in the form of an inclined flat face provided with edges and having the effective width of the rolls on whose undersides magnets are mounted. The channel additionally brings about a homogeneous distribution of the product mass flow coming from the first milling gap and homogeneous loading of the second milling gap.

In the process according to the invention, multistage roll mills are used, preference being given to a stepwise reduction in gap width in product flow direction. Particular preference is given to three-stage roll mills. With increasing number of stages, the particle size distribution becomes narrower. A multistage roll mill in the context of this invention is, for example, a roll mill with a plurality of successive roll pairs or a plurality of successive roll mills with one roll pair each.

In the course of drying, the polymer gel is typically heated to temperatures above the glass transition temperature. Therefore, the dried polymer gel, before being ground, should be cooled below the glass transition temperature and precomminuted. In the case of use of forced air belt driers, this is typically accomplished downstream of a cooling zone, by means of an integrated spiked roll and a roll crusher.

The product mass flow typically still comprises incompletely dried polymer gel. This is preferably removed before the grinding, by means of suitable sieves, for example with a mesh size of 10 mm, comminuted and dried further. Advantageously, incompletely dried polymer gel is removed by means of two sieves of different mesh size, for example 3 mm and 10 mm, and only the coarser particle fraction is comminuted before the further drying.

The temperature of the dried polymer gel supplied to the grinding is preferably from 30 to 100° C., more preferably from 35 to 90° C., most preferably from 40 to 80° C. It is uneconomic to cool the dried polymer gel to an excessive degree. In addition, the polymer gel becomes too brittle, and so the proportion of undesirably small polymer particles in the grinding rises. If the dried polymer gel, in contrast, is too warm, it is still too soft due to the small margin from the glass transition temperature.

The roll mills typically used for grinding have to be protected from the introduction of metallic impurities such as screws or iron filings. This is typically accomplished by means of a magnetic separator. The present invention is based on the finding that such metallic impurities can be removed better after a precomminution in a coarse roll mill. Due to the wider milling gap, the coarse roll mill is less sensitive to these metallic impurities.

The production of the water-absorbing polymer particles is described in detail hereinafter:

The water-absorbing polymer particles are produced by polymerizing a monomer solution or suspension, and are typically water-insoluble.

The monomers a) are preferably water-soluble, i.e. the solubility in water at 23° C. is typically at least 1 g/100 g of water, preferably at least 5 g/100 g of water, more preferably at least 25 g/100 g of water and most preferably at least 35 g/100 g of water.

Suitable monomers a) are, for example, ethylenically unsaturated carboxylic acids, such as acrylic acid, methacrylic acid and itaconic acid. Particularly preferred monomers are acrylic acid and methacrylic acid. Very particular preference is given to acrylic acid.

Further suitable monomers a) are, for example, ethylenically unsaturated sulfonic acids, such as styrenesulfonic acid and 2-acrylamido-2-methylpropanesulfonic acid (AMPS).

Impurities can have a considerable influence on the polymerization. The raw materials used should therefore have a maximum purity. It is therefore often advantageous to specially purify the monomers a). Suitable purification processes are described, for example, in WO 2002/055469 A1, WO 2003/078378 A1 and WO 2004/035514 A1. A suitable monomer a) is, for example, acrylic acid purified according to WO 2004/035514 A1 and comprising 99.8460% by weight of acrylic acid, 0.0950% by weight of acetic acid, 0.0332% by weight of water, 0.0203% by weight of propionic acid, 0.0001% by weight of furfurals, 0.0001% by weight of maleic anhydride, 0.0003% by weight of diacrylic acid and 0.0050% by weight of hydroquinone monomethyl ether.

The proportion of acrylic acid and/or salts thereof in the total amount of monomers a) is preferably at least 50 mol %, more preferably at least 90 mol %, most preferably at least 95 mol %.

The monomers a) typically comprise polymerization inhibitors, preferably hydroquinone monoethers, as storage stabilizers.

The monomer solution comprises preferably up to 250 ppm by weight, preferably at most 130 ppm by weight, more preferably at most 70 ppm by weight, and preferably at least 10 ppm by weight, more preferably at least 30 ppm by weight and especially around 50 ppm by weight, of hydroquinone monoether, based in each case on the unneutralized monomer a). For example, the monomer solution can be prepared by using an ethylenically unsaturated monomer bearing acid groups with an appropriate content of hydroquinone monoether.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers b).

Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 2002/032962 A2.

Preferred crosslinkers b) are pentaerythrityl triallyl ether, tetraallyloxyethane, methylenebismethacrylamide, 15-tuply ethoxylated trimethylolpropane triacrylate, polyethylene glycol diacrylate, trimethylolpropane triacrylate and triallylamine.

Very particularly preferred crosslinkers b) are the polyethoxylated and/or propoxylated glycerols which have been esterified with acrylic acid or methacrylic acid to give di- or triacrylates, as described, for example, in WO 2003/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol, especially the triacrylate of 3-tuply ethoxylated glycerol.

The amount of crosslinker b) is preferably 0.05 to 1.5% by weight, more preferably 0.1 to 1% by weight and most preferably 0.2 to 0.6% by weight, based in each case on monomer a). With rising crosslinker content, the centrifuge retention capacity (CRC) falls and the absorption under a pressure of 21.0 g/cm$^2$ passes through a maximum.

The initiators c) used may be all compounds which generate free radicals under the polymerization conditions, for example thermal initiators, redox initiators, photoinitiators. Suitable redox initiators are sodium peroxodisulfate/ascorbic acid, hydrogen peroxide/ascorbic acid, sodium peroxodisulfate/sodium bisulfite and hydrogen peroxide/sodium bisulfite. Preference is given to using mixtures of thermal initiators and redox initiators, such as sodium peroxodisulfate/hydrogen peroxide/ascorbic acid. The reducing component used is, however, preferably a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Brüggemann Chemicals; Heilbronn; Germany).

Ethylenically unsaturated monomers d) copolymerizable with the ethylenically unsaturated monomers a) bearing acid groups are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate.

The water-soluble polymers e) used may be polyvinyl alcohol, polyvinylpyrrolidone, starch, starch derivatives, modified cellulose, such as methylcellulose or hydroxyethylcellulose, gelatin, polyglycols or polyacrylic acids, preferably starch, starch derivatives and modified cellulose.

Typically, an aqueous monomer solution is used. The water content of the monomer solution is preferably from 40 to 75% by weight, more preferably from 45 to 70% by weight and most preferably from 50 to 65% by weight. It is also possible to use monomer suspensions, i.e. monomer solutions with excess monomer a), for example sodium acrylate. With rising water content, the energy requirement in the subsequent drying rises, and, with falling water content, the heat of polymerization can only be removed inadequately.

For optimal action, the preferred polymerization inhibitors require dissolved oxygen. The monomer solution can therefore be freed of dissolved oxygen before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

Suitable reactors are, for example, kneading reactors or belt reactors. In the kneader, the polymer gel formed in the polymerization of an aqueous monomer solution or suspension is comminuted continuously by, for example, contrarotatory stirrer shafts, as described in WO 2001/038402 A1. Polymerization on the belt is described, for example, in DE 38 25 366 A1 and U.S. Pat. No. 6,241,928. Polymerization in a belt reactor forms a polymer gel which has to be comminuted in a further process step, for example in an extruder or kneader.

To improve the drying properties, the comminuted polymer gel obtained by means of a kneader can additionally be extruded.

The acid groups of the resulting polymer gels have typically been partially neutralized. Neutralization is preferably carried out at the monomer stage. This is typically accomplished by mixing in the neutralizing agent as an aqueous solution or preferably also as a solid. The degree of neutralization is preferably from 25 to 95 mol %, more preferably from 30 to 80 mol % and most preferably from 40 to 75 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts. Particularly preferred alkali metals are sodium and potassium, but very particular preference is given to sodium hydroxide, sodium carbonate or sodium hydrogencarbonate and also mixtures thereof.

However, it is also possible to carry out neutralization after the polymerization, at the stage of the polymer gel formed in the polymerization. It is also possible to neutralize up to 40 mol %, preferably from 10 to 30 mol % and more preferably from 15 to 25 mol % of the acid groups before the polymerization by adding a portion of the neutralizing agent actually to the monomer solution and setting the desired final degree of neutralization only after the polymerization, at the polymer gel stage. When the polymer gel is neutralized at least partly after the polymerization, the polymer gel is preferably comminuted mechanically, for example by means of an extruder, in which case the neutralizing agent can be sprayed, sprinkled or poured on and then carefully mixed in. To this end, the gel mass obtained can be repeatedly extruded for homogenization.

The polymer gel is then preferably dried with a belt drier until the residual moisture content is preferably 0.5 to 15% by weight, more preferably 1 to 10% by weight and most preferably 2 to 8% by weight, the residual moisture content being determined by EDANA recommended test method No. WSP 230.2-05 "Mass Loss Upon Heating". In the case of too high a residual moisture content, the dried polymer gel has too low a glass transition temperature $T_g$ and can be processed further only with difficulty. In the case of too low a residual moisture content, the dried polymer gel is too brittle and, in the subsequent comminution steps, undesirably large amounts of polymer particles with an excessively low particle size are obtained ("fines"). The solids content of the gel before the drying is preferably from 25 to 90% by weight, more preferably from 35 to 70% by weight and most preferably from 40 to 60% by weight. However, a fluidized bed drier or a paddle drier may optionally also be used for drying purposes.

Thereafter, the dried polymer gel is ground and classified, and the apparatus used for grinding may be multistage roll mills, preferably two or three-stage roll mills, pin mills, hammer mills or vibratory mills.

The mean particle size of the polymer particles removed as the product fraction is preferably at least 200 µm, more preferably from 250 to 600 µm and very particularly from 300 to 500 µm. The mean particle size of the product fraction may be determined by means of EDANA recommended test method No. WSP 220.2-05 "Particle Size Distribution", where the proportions by mass of the screen fractions are plotted in cumulated form and the mean particle size is determined graphically. The mean particle size here is the value of the mesh size which gives rise to a cumulative 50% by weight.

The proportion of particles having a particle size of greater than 150 µm is preferably at least 90% by weight, more preferably at least 95% by weight, most preferably at least 98% by weight.

Polymer particles with too small a particle size lower the permeability (SFC). The proportion of excessively small polymer particles ("fines") should therefore be low.

Excessively small polymer particles are therefore typically removed and recycled into the process. This is preferably done before, during or immediately after the polymerization, i.e. before the drying of the polymer gel. The excessively small polymer particles can be moistened with water and/or aqueous surfactant before or during the recycling.

It is also possible to remove excessively small polymer particles in later process steps, for example after the surface postcrosslinking or another coating step. In this case, the excessively small polymer particles recycled are surface postcrosslinked or coated in another way, for example with fumed silica.

When a kneading reactor is used for polymerization, the excessively small polymer particles are preferably added during the last third of the polymerization.

When the excessively small polymer particles are added at a very early stage, for example actually to the monomer solution, this lowers the centrifuge retention capacity (CRC) of the resulting water-absorbing polymer particles. However, this can be compensated for, for example, by adjusting the amount of crosslinker b) used.

When the excessively small polymer particles are added at a very late stage, for example not until an apparatus connected downstream of the polymerization reactor, for example an extruder, the excessively small polymer particles can be incorporated into the resulting polymer gel only with difficulty. Insufficiently incorporated, excessively small polymer particles are, however, detached again from the dried polymer gel during the grinding, are therefore removed again in the course of classification and increase the amount of excessively small polymer particles to be recycled.

The proportion of particles having a particle size of at most 850 µm is preferably at least 90% by weight, more preferably at least 95% by weight, most preferably at least 98% by weight.

The proportion of particles having a particle size of at most 600 µm is preferably at least 90% by weight, more preferably at least 95% by weight, most preferably at least 98% by weight.

Polymer particles of excessively large particle size lower the free swell rate. The proportion of excessively large polymer particles should therefore likewise be small.

Excessively large polymer particles are therefore typically removed and recycled into the grinding of the dried polymer gel.

To further improve the properties, the polymer particles can be surface postcrosslinked. Suitable surface postcrosslinkers are compounds which comprise groups which can form covalent bonds with at least two carboxylate groups of the polymer particles. Suitable compounds are, for example, polyfunctional amines, polyfunctional amido amines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, or β-hydroxyalkylamides, as described in DE 102 04 938 A1 and U.S. Pat. No. 6,239,230.

Additionally described as suitable surface postcrosslinkers are cyclic carbonates in DE 40 20 780 C1,2-oxazolidinone and derivatives thereof, such as 2-hydroxyethyl-2-oxazolidinone, in DE 198 07 502 A1, bis- and poly-2-oxazolidinones in DE 198 07 992 C1, 2-oxotetrahydro-1,3-oxazine and derivatives thereof in DE 198 54 573 A1, N-acyl-2-oxazolidinones in DE 198 54 574 A1, cyclic ureas in DE 102 04 937 A1, bicyclic amide acetals in DE 103 34 584 A1, oxetanes and cyclic ureas in EP 1 199 327 A2 and morpholine-2,3-dione and derivatives thereof in WO 2003/031482 A1.

Preferred surface postcrosslinkers are ethylene carbonate, ethylene glycol diglycidyl ether, reaction products of polyamides with epichlorohydrin and mixtures of propylene glycol and 1,4-butanediol.

Very particularly preferred surface postcrosslinkers are 2-hydroxyethyl-2-oxazolidinone, 2-oxazolidinone and 1,3-propanediol.

In addition, it is also possible to use surface postcrosslinkers which comprise additional polymerizable ethylenically unsaturated groups, as described in DE 37 13 601 A1.

The amount of surface postcrosslinker is preferably 0.001 to 2% by weight, more preferably 0.02 to 1% by weight and most preferably 0.05 to 0.2% by weight, based in each case on the polymer particles.

In a preferred embodiment of the present invention, polyvalent cations are applied to the particle surface in addition to the surface postcrosslinkers before, during or after the surface postcrosslinking.

The polyvalent cations usable in the process according to the invention are, for example, divalent cations such as the cations of zinc, magnesium, calcium, iron and strontium, trivalent cations such as the cations of aluminum, iron, chromium, rare earths and manganese, tetravalent cations such as the cations of titanium and zirconium. Possible counterions are hydroxide, chloride, bromide, sulfate, hydrogensulfate, carbonate, hydrogencarbonate, nitrate, phosphate, hydrogenphosphate, dihydrogenphosphate and carboxylate, such as acetate, citrate and lactate. Salts with different counterions are also possible, for example basic aluminum salts such as aluminum monoacetate or aluminum monolactate. Aluminum sulfate, aluminum monoacetate and aluminum lactate are preferred. Apart from metal salts, it is also possible to use polyamines as polyvalent cations.

The amount of polyvalent cation used is, for example, 0.001 to 1.5% by weight, preferably 0.005 to 1% by weight and more preferably 0.02 to 0.8% by weight, based in each case on the polymer particles.

The surface postcrosslinking is typically performed in such a way that a solution of the surface postcrosslinker is sprayed onto the dried polymer particles. After the spray application, the polymer particles coated with surface postcrosslinker are dried thermally, and the surface postcrosslinking reaction can take place either before or during the drying.

The spray application of a solution of the surface postcrosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers a vertically mounted mixing shaft. Suitable mixers are, for example, horizontal Pflugschar® plowshare mixers (Gebr. Lodige Maschinenbau GmbH; Paderborn; Germany), Vrieco-Nauta continuous mixers (Hosokawa Micron BV; Doetinchem; the Netherlands), Processall Mixmill mixers (Processall Incorporated; Cincinnati; USA) and Schugi Flexomix® (Hosokawa Micron BV; Doetinchem; the Netherlands). However, it is also possible to spray on the surface postcrosslinker solution in a fluidized bed.

The surface postcrosslinkers are typically used in the form of an aqueous solution. The penetration depth of the surface postcrosslinker into the polymer particles can be adjusted via the content of nonaqueous solvent and total amount of solvent.

When exclusively water is used as the solvent, a surfactant is advantageously added. This improves the wetting behavior and reduces the tendency to form lumps. However, preference is given to using solvent mixtures, for example isopropanol/water, 1,3-propanediol/water and propylene glycol/water, where the mixing ratio in terms of mass is preferably from 20:80 to 40:60.

The thermal drying is preferably carried out in contact driers, more preferably paddle driers, most preferably disk driers. Suitable driers are, for example, Hosokawa Bepex® Horizontal Paddle Dryers (Hosokawa Micron GmbH; Leingarten; Germany), Hosokawa Bepex® Disc Dryers (Hosokawa Micron GmbH; Leingarten; Germany), Holo-FMK) driers (Metso Minerals Industries Inc.; Danville; USA) and Nara Paddle Dryers (NARA Machinery Europe; Frechen; Germany). Moreover, fluidized bed driers may also be used.

The drying can be effected in the mixer itself, by heating the jacket or blowing in warm air. Equally suitable is a downstream dryer, for example a shelf drier, a rotary tube oven or a heatable screw. It is particularly advantageous to effect mixing and drying in a fluidized bed drier.

Preferred drying temperatures are in the range of 100 to 250° C., preferably 120 to 220° C., more preferably 130 to 210° C. and most preferably 150 to 200° C. The preferred residence time at this temperature in the reaction mixer or drier is preferably at least 10 minutes, more preferably at least 20 minutes, most preferably at least 30 minutes, and typically at most 60 minutes.

In a preferred embodiment of the present invention, the water-absorbing polymer particles are cooled after the thermal drying. The cooling is preferably performed in contact coolers, more preferably paddle coolers and most preferably disk coolers. Suitable coolers are, for example, Hosokawa Bepex® Horizontal Paddle Coolers (Hosokawa Micron GmbH; Leingarten; Germany), Hosokawa Bepex® Disc Coolers (Hosokawa Micron GmbH; Leingarten; Germany), Holo-Flite® coolers (Metso Minerals Industries Inc.; Danville; USA) and Nara Paddle Coolers (NARA Machinery Europe; Frechen; Germany). Moreover, fluidized bed coolers may also be used.

In the cooler, the water-absorbing polymer particles are cooled to 20 to 150° C., preferably 30 to 120° C., more preferably 40 to 100° C. and most preferably 50 to 80° C.

Subsequently, the surface postcrosslinked polymer particles can be classified again, excessively small and/or excessively large polymer particles being removed and recycled into the process.

To further improve the properties, the surface postcrosslinked polymer particles can be coated or remoisturized.

The remoisturizing is preferably performed at 30 to 80° C., more preferably at 35 to 70° C., most preferably at 40 to 60° C. At excessively low temperatures, the water-absorbing polymer particles tend to form lumps, and, at higher temperatures, water already evaporates to a noticeable degree. The amount of water used for remoisturizing is preferably from 1 to 10% by weight, more preferably from 2 to 8% by weight and most preferably from 3 to 5% by weight. The remoisturizing increases the mechanical stability of the polymer particles and reduces their tendency to static charging. The remoisturizing is advantageously performed in the cooler after the thermal drying.

Suitable coatings for improving the free swell rate and the permeability (SFC) are, for example, inorganic inert substances, such as water-insoluble metal salts, organic polymers, cationic polymers and di- or polyvalent metal cations. Suitable coatings for dust binding are, for example, polyols. Suitable coatings for counteracting the undesired caking tendency of the polymer particles are, for example, fumed silica, such as Aerosil® 200, and surfactants, such as Span® 20.

The water-absorbing polymer particles produced by the process according to the invention have a moisture content of preferably 0 to 15% by weight, more preferably 0.2 to 10% by weight and most preferably 0.5 to 8% by weight, the moisture content being determined by EDANA recommended test method No. WSP 230.2-05 "Mass Loss Upon Heating".

The water-absorbing polymer particles produced by the process according to the invention have a proportion of particles having a particle size of 300 to 600 µm of preferably at least 30% by weight, more preferably at least 50% by weight, most preferably at least 70% by weight.

The water-absorbing polymer particles produced by the process according to the invention have a centrifuge retention capacity (CRC) of typically at least 15 g/g, preferably at least 20 g/g, more preferably at least 22 g/g, especially preferably at least 24 g/g and most preferably at least 26 g/g. The centrifuge retention capacity (CRC) of the water-absorbing polymer particles is typically less than 60 g/g. The centrifuge retention capacity (CRC) is determined by EDANA recommended test method No. WSP 241.2-05 "Fluid Retention Capacity in Saline, After Centrifugation".

The water-absorbing polymer particles produced by the process according to the invention have an absorption under a pressure of 49.2 g/cm² of typically at least 15 g/g, preferably at least 20 g/g, more preferably at least 22 g/g, especially preferably at least 24 g/g and most preferably at least 26 g/g. The absorption under a pressure of 49.2 g/cm² of the water-absorbing polymer particles is typically less than 35 g/g. The absorption under a pressure of 49.2 g/cm² is determined analogously to EDANA recommended test method No. WSP 242.2-05 "Absorption Under Pressure, Gravimetric Determination", except that a pressure of 49.2 g/cm² is established instead of a pressure of 21.0 g/cm².

The EDANA test methods are obtainable, for example, from EDANA, Avenue Eugene Plasky 157, B-1030 Brussels, Belgium.

EXAMPLES 89.5 g of acrylic acid, 805.6 g of a 37.3% by weight aqueous sodium acrylate solution, 97.3 g of deionized water and 1.60 g of 3-tuply ethoxylated glyceryl triacrylate (approx. 85% strength by weight) were freed of dissolved atmospheric oxygen by introducing nitrogen for 30 minutes. The polymerization was initiated in a 2 liter plastic vessel by adding 1.5 g of sodium peroxodisulfate (30.0% by weight aqueous solution), 2.0 g of ascorbic acid (0.48% by weight aqueous solution) and 2.5 g of hydrogen peroxide (0.11% by weight aqueous solution).

800 g of the polymer gel were comminuted by means of an extruder with a 6 mm die plate. 2.00 g of iron filings, which had been turned irregularly in terms of longitudinal direction but for the most part were in spiral form, had a mean length of about 2 to 5 mm (extended iron filing) and had a mean thickness of about 0.1 mm, were distributed homogeneously on the flattened surface of about one third of the polymer gel (layer thickness of the comminuted polymer gel approx. 1 to 2 cm). A second third of polymer gel was first layered on top with comparable layer thickness, another 2.00 g of iron filings were distributed homogeneously thereon, and finally the third third of polymer gel was layered on top as before. Subsequently, all of the polymer gel was cautiously mixed manually, such that excessive iron filing accumulation was not observed in any region, and then extruded again.

The polymer gel laden with iron filings was dried at 150° C. for 60 minutes and ground on a roll mill with a set gap width of 2000 µm. This gave polymer particles (type A), a portion of which was ground again on the roll mill, but this time with a set gap width of 1000 µm, to give polymer particles (type B).

The polymer particles (type A) were classified through a 1700 µm sieve and the particles remaining on the sieve were separated with a magnet from the particles without iron filings and used as particles (type A1) for the subsequent tests.

The polymer particles (type B) were classified through a 1700 µm and a 1000 µm sieve and the particles remaining on the 1000 µm sieve were separated with a magnet from the particles without iron filings and used as particles (type B1) for the subsequent tests.

At the upper end of a smooth plastic sheet arranged at an angle of inclination of 31°, polymer particles (type A1 and B1) were applied in one motion from a height of 16 cm through a slot-shaped shaft over a width of 8 cm. In the downward direction of the sheet, commencing from 5.5 cm away from the application line, round magnets with a diameter of 3 cm were arranged below the plastic sheet in three staggered rows in close succession over the total width, which was delimited by side walls to 11 cm.

The mass of the polymer particles removed by means of the magnet, and also the mass of those not removed, was determined gravimetrically.

TABLE 1

Mass balance of the polymer particles of type A1

| Starting weight [g] | Particles removed [g] | Particles not removed [g] | Particles removed [%] | Particles not removed [%] |
|---|---|---|---|---|
| 1.0321 | 0.6380 | 0.3942 | 61.8 | 38.2 |
| 1.0575 | 0.6476 | 0.4099 | 61.2 | 38.8 |
| 1.0057 | 0.6007 | 0.4053 | 59.7 | 40.3 |
| 1.0407 | 0.7156 | 0.3253 | 68.8 | 31.3 |
| 1.0457 | 0.6122 | 0.4333 | 58.5 | 41.4 |
| 1.0586 | 0.6062 | 0.4521 | 57.3 | 42.7 |
| 1.0365 | 0.5784 | 0.4577 | 55.8 | 44.2 |
| 1.0323 | 0.7861 | 0.2461 | 76.2 | 23.8 |
| 1.0339 | 0.6181 | 0.4158 | 59.8 | 40.2 |
| 1.0058 | 0.6300 | 0.3767 | 62.6 | 37.5 |
| Mean values: | | | 62.2 | 37.8 |

TABLE 1-continued

Mass balance of the polymer particles of type A1

| Starting weight [g] | Particles removed [g] | Particles not removed [g] | Particles removed [%] | Particles not removed [%] |
|---|---|---|---|---|

TABLE 2

Mass balance of the polymer particles of type B1

| Starting weight [g] | Particles removed [g] | Particles not removed [g] | Particles removed [%] | Particles not removed [%] |
|---|---|---|---|---|
| 1.0192 | 0.9296 | 0.0896 | 91.2 | 8.8 |
| 0.9927 | 0.8872 | 0.1056 | 89.4 | 10.6 |
| 1.0386 | 0.8760 | 0.1621 | 84.3 | 15.6 |
| 1.0461 | 0.8638 | 0.1825 | 82.6 | 17.4 |
| 1.0652 | 0.9423 | 0.1215 | 88.5 | 11.4 |
| 1.0441 | 0.8703 | 0.1708 | 83.4 | 16.4 |
| 1.0915 | 0.9656 | 0.1263 | 88.5 | 11.6 |
| 1.0589 | 0.9344 | 0.1247 | 88.2 | 11.8 |
| 1.0182 | 0.8975 | 0.1183 | 88.1 | 11.6 |
| 0.9988 | 0.8464 | 0.1525 | 84.7 | 15.3 |
| Mean values: | | | 86.9 | 13.0 |

At the end of the test procedure, the particles were pulverized to check their loading with filings. In >95% of the particles, one iron filing per particle was found.

The tests demonstrate that the separation rate increases when the polymer particles are precomminuted by means of a coarse roll mill.

The invention claimed is:

1. A process for producing water-absorbing polymer particles by polymerizing a monomer solution or suspension comprising
   a) at least one ethylenically unsaturated monomer which bears an acid group and may be at least partly neutralized,
   b) at least one crosslinker,
   c) at least one initiator,
   d) optionally one or more ethylenically unsaturated monomer copolymerizable with the monomer mentioned under a), and
   e) optionally one or more water-soluble polymer, drying a resulting polymer gel, and grinding and classifying the dried polymer gel, wherein the grinding is performed using a multistage roll mill, a first milling gap having a gap width of 500 to 5000 µm, a product mass flow passing through the first milling gap is conducted through a magnetic separator to a second milling gap, and the second milling gap has a smaller gap width than the first milling gap.

2. The process according to claim 1, wherein the multistage roll mill has at least three different milling gaps.

3. The process according to claim 1, wherein the polymer gel is dried on a forced air belt drier.

4. The process according to claims 1, wherein the dried polymer gel is precomminuted before the grinding.

5. The process according to claim 1, wherein an incompletely dried polymer gel is removed before the grinding.

6. The process according to claims 1, wherein the dried polymer gel supplied to the grinding has a particle size of at most 10 mm.

7. The process according to claim 1, wherein the dried polymer gel supplied to the grinding has a temperature of 40 to 80° C.

8. The process according to claims 1, wherein the monomer a) is acrylic acid partly neutralized to an extent of at least 50 mol %.

9. The process according to claim 1, wherein the monomer a) has been neutralized to an extent of 25 to 85 mol %.

10. The process according to claim 1, wherein the water-absorbing polymers have a centrifuge retention capacity of at least 15 g/g.

* * * * *